United States Patent [19]

Bryant

[11] Patent Number: 4,621,646
[45] Date of Patent: Nov. 11, 1986

[54] BLOOD FLOW MEASURING METHOD

[75] Inventor: Gordon H. Bryant, Kailua, Hi.

[73] Assignee: The United States of America as represented by the Secretary of the Army, Washington, D.C.

[21] Appl. No.: 561,774

[22] Filed: Dec. 15, 1983

[51] Int. Cl.⁴ .............................................. A61B 5/02
[52] U.S. Cl. ..................... 128/692; 128/673
[58] Field of Search ................... 128/205.23, 656–658, 128/675, 691, 692, 672–674, 687; 604/118

[56] References Cited

U.S. PATENT DOCUMENTS

| | | | |
|---|---|---|---|
| 3,437,088 | 4/1969 | Bielinski | 604/118 |
| 3,448,739 | 6/1969 | Stark et al. | 128/656 |
| 3,592,183 | 7/1971 | Watkins | 604/118 |
| 4,137,906 | 2/1979 | Akiyama et al. | 128/657 |
| 4,148,307 | 4/1979 | Utsugi | 128/4 |
| 4,150,676 | 4/1979 | Jackson | 128/657 |
| 4,213,461 | 7/1980 | Pevsner | 128/656 |
| 4,217,911 | 8/1980 | Layton | 604/118 |
| 4,263,917 | 4/1981 | Moss | 128/656 |
| 4,299,226 | 11/1981 | Banka | 128/657 |
| 4,508,103 | 4/1985 | Calisi | 128/673 |

Primary Examiner—Edward M. Coven
Assistant Examiner—Max F. Hindenburg
Attorney, Agent, or Firm—John H. Raubitschek; Francis A. Cooch; Arthur L. Spechler

[57] ABSTRACT

An illustrative embodiment of the invention measures blood flow through a vein or an artery. A balloon catheter is inserted into the vessel and is inflated until the balloon temporarily stops blood flow in order to measure the diameter of the vessel. The balloon is deflated a bit to reestablish flow through the vessel in the annulus that is formed between the outer surface of the balloon and the adjacent surface of the vessel. Apertures in the catheter on opposite ends of the balloon establish fluid communication with the blood to permit the change in blood pressure to be measured as it flows through the annulus in order to derive the blood flow in milliliters per minute (ml/min) or in some other suitable parameter.

2 Claims, 2 Drawing Figures

BLOOD FLOW MEASURING METHOD

BACKGROUND OF THE INVENTION

1. Field of Invention

This invention relates to surgical procedures and instruments and, more particularly, to method and apparatus for measuring the flow of blood through a vessel by observing the change in blood pressure as it flows past a balloon catheter, and the like.

2. Description of the Prior Art

To measure blood flow in veins and arteries, a bolus of cool, normal saline solution is injected into the vessel under observation. The bolus, injected at a temperature that is lower than the blood temperature, mixes with the blood, and the temperature of the mixture is sensed through multiple thermistor catheters. The observed temperature increase in the bolus is related, in general, to the blood flow in terms of, for example, milliliters per minute. The temperature change, however, is also relates to a number of other factors that are entirely independent of the blood flow. For example, the temperature of the bolus will change between the injection site and the thermistors; the temperature difference between the blood and the injectate can vary; and the volume of the injected bolus also can vary. These, and possibly other effects combine to produce errors in the accuracy of the flow measurement that can be as great as ±10%.

Not only is this prior art technique inaccurate, but it also requires a minimum of three injections to produce an average value of blood flow that will provide this ±10% accuracy. Inaccuracy aside, perhaps the most undesirable feature of this prior art technique is the risk to the patient inherent in injecting foreign material into the circulatory system.

Unquestionably, there is a need for a more accurate blood flow measuring technique that does not required extensive surgery or injecting foreign matter into the pateint.

SUMMARY OF INVENTION

These and other problems that have characterized the prior art are overcome, to a great extent, through the practice of the invention. Thus, in accordance with the invention, a balloon catheter is inserted into the blood vessel under consideration. The balloon is inflated until the flow of blood within the vessel stops, as determined for example, through a decrease in blood pressure to zero observed through a pressure sensing means, or port, on the catheter that is downstream from the section of maximum balloon inflation. The diameter or cross section area of the blood vessel at the place of examination can then be identified through a suitable calibration table prepared from a number of earlier tests conducted with passagways of known size.

The balloon is deflated slightly to establish an annular passageway between the outer surface of the balloon and the adjacent surface of the blood vessel. Blood now flows through this passageway and, being a fluid, obeys the usual laws of fluid dynamics. The blood pressure in the annulus, for instance, decreases relative to the pressure upstream from the annulus.

Measuring these two pressures at sensing ports upstream and downstream from the annulus, and calculating their difference, provides a basic piece of data from which the blood flow as a function of volume per unit time can be determined. Naturally, although the upstream and downstream pressures are measured in the illustrative embodiment of the invention through pressure gage or manometer sensing ports, almost any device for registering fluid pressure differences within a blood vessel to an acceptable degree of accuracy will be suitable for this application.

By comparing this pressure difference data with predetermined graphs of blood flow as a function of balloon diameter for a range of vessel diameters, the correct blood flow in volume per unit time can be identified.

The manometer ports, moreover, provide the further capability of enabling blood specimens to be withdrawn from the circulatory system in the immediate vicinity of the flow measurement for further study.

Clearly, the technique embodied in this invention is a significant improvement over the prior art. Foreign matter, e.g., saline solution, is not added to the blood stream, thereby, reducing the degree of risk to the patient. The balloon catheter structure, moreover, is simple and reliable. The need to introduce electrical temperature sensing apparatus into the circulatory system is also avoided through the practice of the invention. All of these foregoing advantages are attained through a method and apparatus that measures blood flow with significantly enhanced accuracy.

These and other features of the invention will be appreciated in more complete detail through a study of the following description of preferred embodiments of the invention, when taken with the figures of the drawing. The scope of the invention, however, is limited only through the claims appended hereto.

DESCRIPTION OF THE PREFERRED EMBODIMENTS OF THE INVENTION

Figures 1, 2:
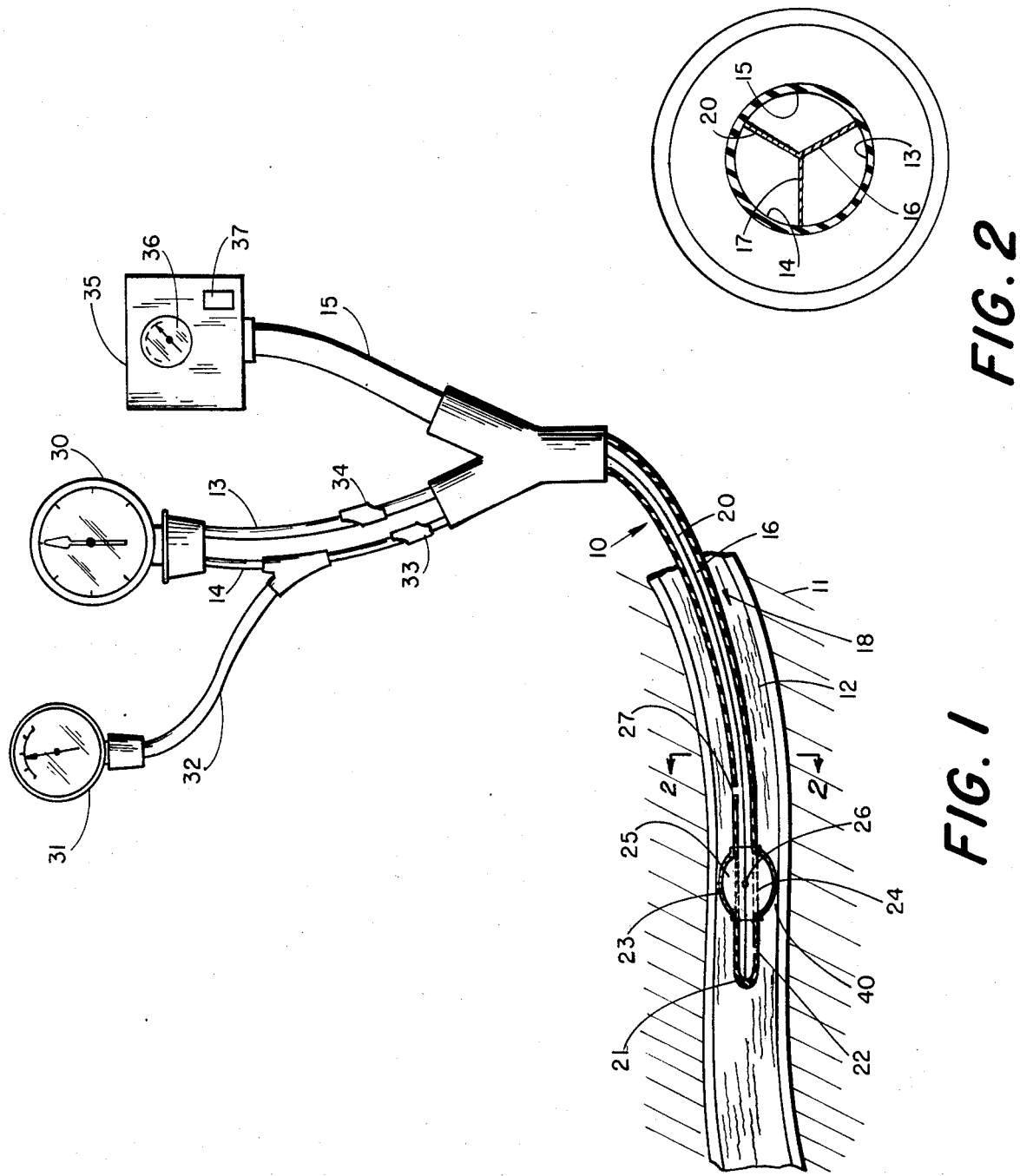
FIG. 1 is a front elevation in full section of a typical embodiment of the invention.
FIG. 2 is a transverse view, in full section, of the device shown in FIG. 1, taken along the line 2—2 in FIG. 1 and viewed in the direction of the arrows.

For a more detailed understanding of the invention, attention is invited to FIG. 1 which shows a generally tubular catheter 10 of flexible material. The catheter 10 is inserted into a blood vessel 11 through a suitable incision (not shown) and lodged within the blood vessel at the location in which it is desired to measure the flow of blood 12.

As illustrated in FIG. 2, the catheter 10 has three internal conduits 13, 14 and 15, each of which is fluid tight. The conduits 13, 14 and 15 are formed, moreover, by means of flexible partitions 16, 17 and 20 which extend through the entire length of the catheter 10. For descriptive purpose, the direction of blood flow within the vessel 11 is illustrated by means of an arrow 18, shown in FIG. 1.

The terminal portion of the catheter 10 that protrudes downstream into the blood vessel 11 is capped with an hemispherical fairing 21 to ease the insertion of the catheter into the blood vessel. The fairing 21 is pierced by a downstream pressure sensing means, or aperture 22 that establishes fluid communication between the blood 12 in the vessel 11 and the conduit 14 (FIG. 2). An inflatable balloon 23 is secured to the outer surface of a catheter shank 24 in a fluid-tight manner in order to establish a selectively inflatable chamber 25 in the torus that is formed between the inner surface of the balloon and the outer surface of the shank. Fluid communication also is provided between the inflatable chamber 25 and the conduit 15 by means of a port 26 that penetrates the shank 24.

An upstream pressure sensing means, or aperture 27 is formed in the catheter 10 between the upstream end of the balloon 23 and the catheter incision (not shown) in the blood vessel 11. As illustrated, the upstream aperture 27 enables the blood 12 to flow into the conduit 13. The conduits 13, 14 are coupled to a differential pressure manometer, gage, or sensing means 30. Although shown only for illustrative purposes as a gage that measures the difference between the blood pressure sensed at the downstream aperture 22 and the blood pressure at the upstream aperture 27, any differential pressure transducer adaptable to the physical environment under consideration is suitable for use in connection with the invention.

For reasons described subsequently in more complete detail, a blood pressure gage 31 also is coupled through a conduit 32 to the conduit 14 in order to register directly the blood pressure, if any, at the downstream pressure sensing aperture 22. A blood sampling valve 33 also is connected to the conduit 14 to permit a specimen of the blood that flows into the downstream aperture to be drawn off for further testing. In a similar manner, a valve 34 enables flow specimens to be drawn from the conduit 13 after entering that conduit through the upstream aperture 27.

The conduit 15, moreover, establishes the means for selectively inflating the balloon 23 with a suitable fluid, e.g., water or air, by means of pump 35 that is coupled to the end of the conduit 15 external to the blood vessel 11. A pressure gage 36 registers the pressure of the inflating fluid within the conduit 15, as described subsequently in more complete detail. Naturally, the conduit 15 and the pump 35 are provided with suitable pressure relief means 37 in order to control the deflation of the balloon 23.

In operation, the catheter 10 is inserted through an incision (not shown), into the blood vessel 11 and is lodged in a desired, predetermined location by observing, for example, graduations on the catheter that measure the length the catheter has travelled through the blood vessel. When in place, the pump 35 is activated to inflate the balloon 23 to a degree that just completely obstructs the flow of the blood 12 through the vessel 11. Complete obstruction of the blood vessel 11 is registered by noting the downstream blood pressure registered on the gage 31. When the blood pressure gage 31 indicates zero blood pressure downstream from the balloon 23, it can be assumed that the flow of blood past the balloon 23 has stopped and that the maximum circumference of the balloon matches the corresponding circumference of the adjacent part of the blood vessel 11.

In this manner, the inflation pressure of the balloon can be directly related to the transverse cross-section area of the blood vessel 11 in the vicinity of the measurement by comparison with a calibration table of inflation pressure as a function of vessel diameters for various size balloon catheters.

The balloon 23 is slightly deflated by manipulating the pressure relief means 37 to form a thin annulus 40 between the outer balloon surface and the adjacent portion of the wall of the blood vessel 11. Flow of the blood 12 past the balloon 23 is reestablished in this manner in order to enable the upstream and downstream pressure difference to be measured. Illustratively, the blood upstream flows into the pressure sensing aperture 27 and downstream blood (at a measurably lower pressure) flows into the pressure sensing aperture 22. Blood, taken into the measuring system in the foregoing manner, fills the conduits 13 and 14, respectively and these blood pressures are registered by the differential pressure sensing means 30 to produce a measurement of the difference between the pressures of the blood 12 as observed upstream and downstream relative to the balloon 23.

As previously mentioned, the measured pressure difference can be compared with calibration graphs that relate blood vessel diameter and balloon diameter to blood flow in, for instance, milliliters per minute, the diameter of the blood vessel having been determined through the preceeding step of temporarily terminating flow through the vessel. Should it be appropriate, specimens of the upstream and downstream blood can be taken through the valves 34 and 33, respectively.

By way of general background, it will be recalled that blood, being a fluid, responds to conventional fluid dynamic analysis. Accordingly, as applied to this invention, it is believed that the following equation defines the theoretical basis for the invention and establishes the relationship between the blood pressure difference, the blood vessel diameter and the balloon diameter:

$$Q = ACd(2g\Delta h)^{\frac{1}{2}}$$

where
Q = Flow
A = Area of annulus between the balloon and the blood vessel
g = Gravitational acceleration
$\Delta h$ = Upstream and downstream blood pressure difference
Cd = Coefficient of discharge, the ratio of area of annulus A to the blood vessel diameter.

Thus, there is provided in accordance with the invention a technique for measuring blood flow to a higher degree of accuracy than that which has heretofore been attainable without extensive surgery or subjecting the patient to excessive risk through the introduction of saline solution into the circulatory system. The invention is, of course, subject to a number of modifications, of which, typically, an automatic direct read-out in blood pressure can be substituted for reference to the calibration graphs and data described above.

I claim:

1. A method for measuring blood flow within a blood vessel comprising the steps of, inserting a catheter into the blood vessel, said catheter having a balloon which when inflated establishes an upstream and downstream side of said balloon, inflating said balloon on said catheter to contact the adjacent blood vessel walls to temporarily terminate blood flow through the blood vessel, determining the diameter of said blood vessel, partially deflating said balloon to enable the blood to flow through an annulus formed between said partially deflated balloon and the adjacent blood vessel wall, determining the diameter of said balloon, determining the area of said annulus from said blood vessel diameter and said catheter balloon diameter, recording the dynamic pressure on said upstream side of said balloon, recording the dynamic pressure on said downstream balloon side to establish the pressure difference in the blood upstream and downstream of said annulus, and determining the blood flow in response to said annulus area and blood pressure difference.

2. A method according to claim 1 comprising the further step of drawing at least one blood specimen from the blood vessel in the vicinity of said balloon.

* * * * *